United States Patent [19]
Freilich et al.

[11] Patent Number: 6,004,818
[45] Date of Patent: Dec. 21, 1999

[54] AGGREGOMETER WITH DISPOSABLE TEST CELL

[75] Inventors: Arthur H. Freilich, Ardmore; Nicholas J. Veriabo, Springfield; Andrew M. Roth, Landsdowne, all of Pa.

[73] Assignee: Chrono-Log Corporation, Havertown, Pa.

[21] Appl. No.: 08/906,634

[22] Filed: Aug. 7, 1997

[51] Int. Cl.⁶ .................................................. G01N 33/86
[52] U.S. Cl. ......................... 436/69; 436/149; 436/150; 436/151; 422/73; 422/82.01; 422/82.02; 73/64.41; 600/369
[58] Field of Search .............................. 436/63, 69, 149, 436/150, 151; 422/68.1, 73, 82.01, 82.02; 324/446, 449; 600/368, 369

[56] References Cited

U.S. PATENT DOCUMENTS

| | | | |
|---|---|---|---|
| 2,555,937 | 6/1951 | Rosenthal et al. | 324/443 |
| 4,319,194 | 3/1982 | Cardinal et al. | 324/449 |
| 4,591,793 | 5/1986 | Freilich | 324/446 |
| 4,822,568 | 4/1989 | Tomita | 422/73 |
| 5,601,995 | 2/1997 | Exner | 435/13 |

Primary Examiner—Maureen M. Wallenhorst
Attorney, Agent, or Firm—Caesar, Rivise, Bernstein, Cohen & Pokotilow, Ltd.

[57] ABSTRACT

An aggregometer which is economical and accurate is provided. The aggregometer includes a disposable test cell having two electrode tips. Adjacent parallel planar surfaces of the electrode tips define a channel which is substantially parallel to a flow direction of the sample prior to entering the channel. Also provided is a method for analyzing platelet aggregation by measuring electrical impedance in a sample using the aggregometer.

15 Claims, 2 Drawing Sheets

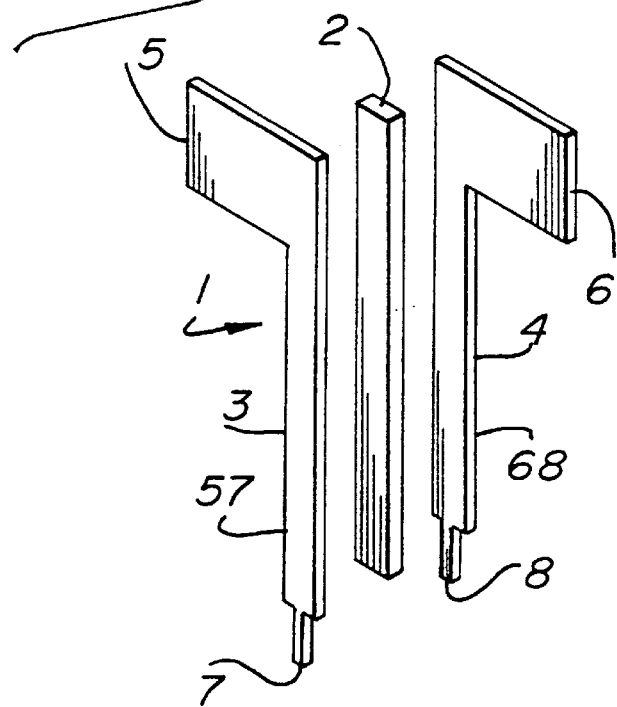
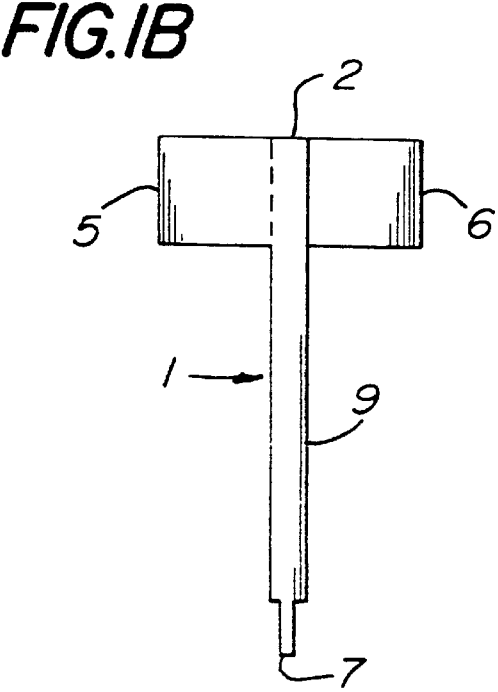
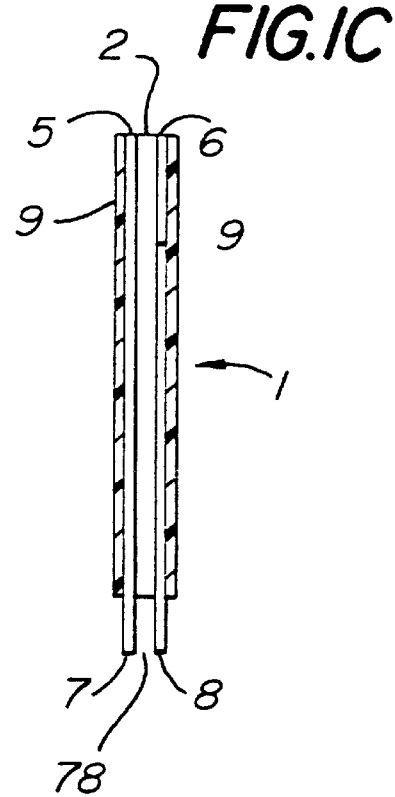

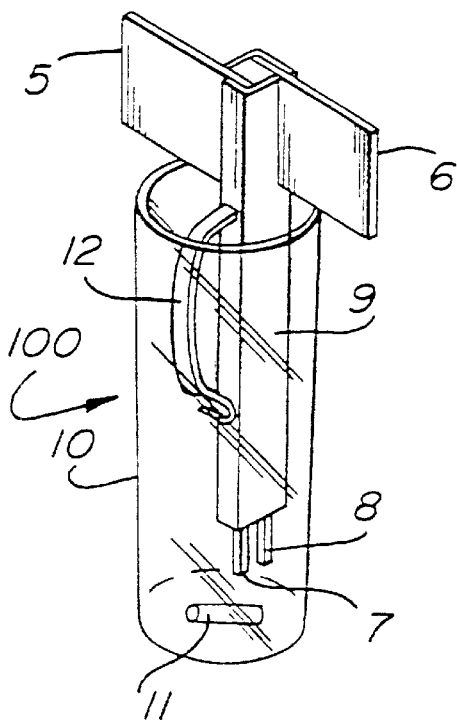
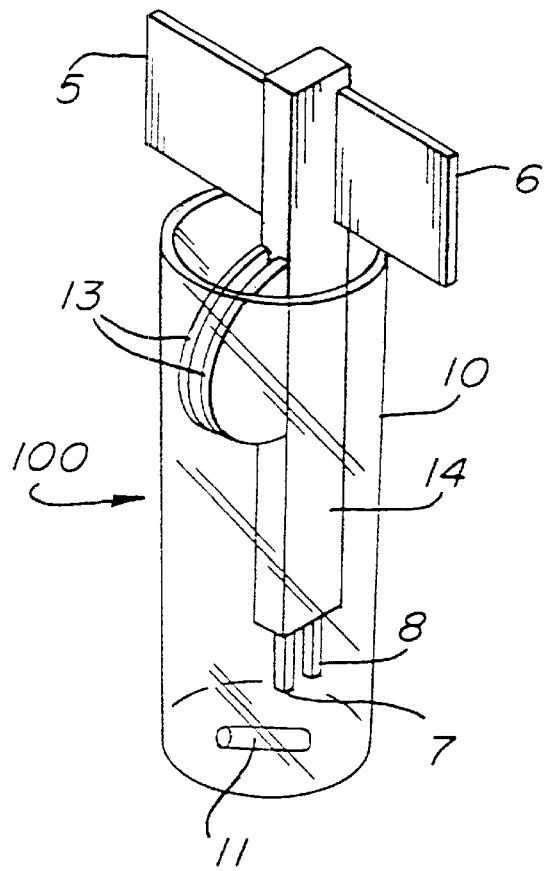
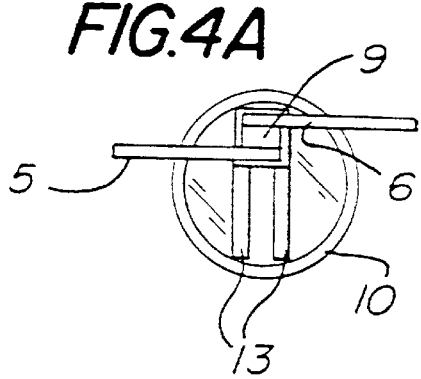
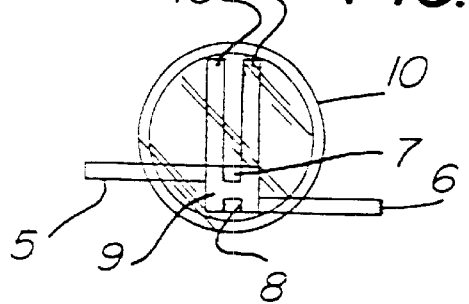

AGGREGOMETER WITH DISPOSABLE TEST CELL

FIELD OF THE INVENTION

This invention relates to a method of, and a disposable apparatus for, monitoring blood platelet aggregation.

BACKGROUND OF THE INVENTION

Blood consists of cells suspended in a protein rich fluid called plasma. There are three major groups of cells in blood: red cells, white cells and platelets. Platelets can, when they come into contact with certain materials and chemicals (especially those released from damaged cells), undergo a process known as the aggregation-adhesion reaction. When they aggregate, platelets change from a discoid shape to a more spherical form, extend long processes known as pseudopodia and become sticky. As a result, the platelets stick to one another and to the damaged tissue, thus plugging gaps or holes in the blood vessel wall. Although the primary response of platelets is to aggregate, a secondary release reaction may also occur, during which platelets release materials which accelerate the clotting process.

The phenomenon of aggregation is a widely studied property of platelets. It is of interest not only for scientific reasons since, inter alia, platelets make an ideal test system for examining cellular mechanisms and drug action, but also has diagnostic significance since there are many conditions in which platelet function is abnormal, and screening of platelet function is a common hematological test. Instruments used to analyze aggregation are known as aggregometers.

An early development in the aggregometer art was the Born aggregometer. The Born aggregometer analyzes aggregation response in samples of platelet-rich plasma (PRP) by measuring light transmission through the sample. In untreated PRP, the majority of the light is scattered by the platelets and transmission is minimal. On the other hand, when an aggregating agent is added to the stirred sample, the platelets clump together and light transmission increases. One serious drawback of the Born aggregometer, and conventional optical aggregometers in general, is the necessity to first separate the blood by centrifugation to obtain samples of PRP and platelet poor plasma (PPP).

Another type of device for analyzing aggregation is the to membrane capacitance aggregometer, in which a change in capacitance between two electrodes resulting from platelet aggregation is measured. However, measurement of capacitance, or even change in capacitance in the capacitance range in question, is difficult, and such an apparatus tends to be prone to drift and disturbance by outside influences.

U.S. Pat. No. 4,319,194 to Cardinal et al. discloses an aggregometer which analyzes platelet aggregation by passing a very small electric current between two electrodes immersed in a sample of blood or PRP and measuring the electrical impedance between the electrodes. During initial contact with the blood or PRP, the electrodes become coated with a monolayer of platelets. When an aggregating agent is added, platelets gradually accumulate on the monolayer coating, increasing the impedance between the electrodes. The change in impedance is recorded as a function of time.

Cardinal et al. eliminated the need to centrifuge blood to obtain PRP and PPP for use in measuring aggregation of platelets optically. The ability to speed-up testing, reduce labor costs, and test the platelets in their natural milieu was an important advance in platelet studies. The measurement in whole blood also allows studies to be performed in cases where optical aggregation is not reliable, such as with giant platelets (Bernard-Soulier syndrome), where red cells have been lysed or where it is difficult to obtain enough blood to make PRP and PPP, such as with small animals or babies.

The aggregometer of Cardinal et al. employs round or rod-shaped wires as electrodes, failing to appreciate certain disadvantages of these wires. The wires are pliable and unless attached at both ends, there can be movement of the wires during handling and cleaning, causing inconsistent results. The shapes of the electrodes and supporting structure cause variations in the flow pattern from electrode to electrode. These variations require testing and matching of electrodes, which increase the manufacturing costs. Each electrode requires exact placement of the wires during fabrication, making the final product expensive and therefore not disposable after each test.

Cardinal et al. prefers that the electrodes comprise precious metals since base metals drift in blood/saline mixtures; however, precious metal electrodes are too expensive to be disposable. Therefore, the electrode assembly must be cleaned by hand between tests, exposing the operator to contact with the sample, and thus potentially exposing the operator to diseases transmitted through the fluids contained in the sample. Since diseases such as hepatitis and AIDS can be transmitted through handling of blood products, there is an understandable reluctance on the part of medical professionals to handle blood, blood products and objects contaminated therewith.

U.S. Pat. No. 4,591,793 to Freilich addresses at least some of the foregoing problems by substituting for the wire electrodes a conductive ink printed on a plastic nonreactive base. This device is less expensive than the Cardinal et al. device and is disposable after each test; however, there are disadvantages to the Freilich device as well. The platelets have difficulty adhering to the exposed conductive surface of the Freilich device, probably due to the surface being thin. Sometimes the aggregated platelets break off the surface, causing a sudden change in impedance. Although the Freilich device is inexpensive to manufacture, the measurements returned by the device are inconsistent and not reproducible.

Accordingly, there is a need for a disposable, but accurate and reliable, platelet aggregation measuring system in which the items that contact the sample, such as the cuvette, the electrode and the stirring agitator, are discarded after a single use, particularly in clinical applications. With a single-use disposable system, it is not necessary to retrieve, cleanse and re-use the electrode assembly and/or other items such as the stir bar that have been in contact with the blood.

SUMMARY OF THE INVENTION

The present invention provides a method of and disposable apparatus for monitoring platelet aggregation which avoid at least the aforementioned disadvantages of the previous optical and membrane capacitance aggregometers.

The method of monitoring blood-platelet aggregation in a platelet-containing sample comprises the step of monitoring the to change in electrical resistance between electrodes in the sample while relative movement of the sample and electrodes occurs, wherein the electrodes are shafts having tips that are non-circular in cross-section.

The apparatus for monitoring blood-platelet aggregation comprises: a cuvette for holding a platelet-containing sample; a means for stirring the sample; at least two electrodes and associated means for mounting them in predetermined positions with respect to one another in the cuvette, wherein the electrodes are shafts having tips that are non-circular in cross-section; a power source for supplying electric current to the electrodes; and a data analysis device for receiving and analyzing the change in electrical resistance or impedance between the electrodes.

BRIEF DESCRIPTION OF THE DRAWINGS

The invention will be described in conjunction with the following drawings in which like reference numerals designate like elements and wherein:

FIG. 1A is a front view of the components of an embodiment of an electrode assembly according to the invention;

FIG. 1B is a front view of an electrode assembly assembled from the components depicted in FIG. 1A;

FIG. 1C is a side view of the electrode assembly depicted in FIG. 1B with the coating partially broken away;

FIG. 2 is an isometric view of an embodiment of an aggregometer test cell according to the invention;

FIG. 3 is an isometric view of another embodiment of an aggregometer test cell according to the invention;

FIG. 4A is an overhead view of the aggregometer test cell shown in FIG. 3; and

FIG. 4B is a bottom view of the aggregometer test cell shown in FIG. 3.

DETAILED DESCRIPTION OF PREFERRED EMBODIMENTS

The inventors have found that variations in stirring and flow of the sample around the electrodes result in variations in measurements. The speed of the sample stirring, the force of the platelets as they move past the electrode and the flow pattern changes caused by the electrode assembly are all important factors in measuring aggregation. The electrode assembly according to the invention facilitates a reproducible flow pattern around it and has a minimum effect on the platelets sticking to it.

A number of electrode assembly configurations were explored; however, the inventors discovered that the most reproducible configuration has the electrodes side-by-side with respect to the flow pattern. This configuration allows the platelets to stick to the face and the area between the electrodes, facilitating the formation of a bridge of platelets between the electrodes, which results in a stronger bond of platelets to the electrodes. Therefore, the platelet buildup on the electrodes is less likely to be displaced by the force of the sample stirring.

FIGS. 1A, 1B and 1C depict a preferred electrode assembly 1 of the invention, wherein an insulator 2 is sandwiched between two flag-shaped electrodes 3 and 4. The insulator can comprise any non-conducting material, such as mylar, plastic or teflon, which will separate the electrodes by the proper amount. Teflon is a preferred material. Electrode 3 includes connection tab 5 at one end and tip 7 at the other end thereof, with a shaft 57 joining the tab 5 and tip 7. Electrode 4 includes connection tab 6 at one end and tip 8 at the other end thereof, with a shaft 68 joining the tab 6 and tip 8. After joining the electrodes 3 and 4 and insulator 2, a non-conductive coating 9 is applied to the insulator 2 and electrode shafts 57 and 68 (i.e., the coating 9 is applied to the insulator 2 and electrodes 3 and 4 on all but the tabs 5 and 6 and tips 7 and 8 thereof). The non-conductive coating can comprise any insulating material, such as plastic or epoxy, which is non-reactive with the blood sample. A preferred material is polystyrene or other suitable plastic.

As shown in FIGS. 2 and 3, the electrode assembly 1 is fixed within a cuvette 10 such that the tips 7 and 8 are preferably both placed along a single radius from the center of the cuvette 10 to the wall of the cuvette 10. The cuvette can be comprised of any medical grade plastic, which is non-reactive with blood. Polystyrene is a preferred material.

Prior to and during measurement, a stir bar 11 is activated to generate a circular flow of sample (not shown) within the cuvette 10. The stir bar can comprise a teflon coated stir bar, steel or siliconized steel. Siliconized stainless steel is the preferred material.

Thus, the electrode tips 7 and 8 are substantially side-by-side (along a radius) with respect to the flow pattern, which as mentioned above is an advantageous configuration. The adjacent planar surfaces of the electrode tips 7 and 8 define a channel 78 which is preferably substantially parallel to a flow direction of the sample prior to entering the channel. The expression "substantially parallel" in the context of this invention means that the items being compared are within about ±20° of being perfectly parallel. Reproducibility diminishes as the angle increases, due to turbulent variable flow patterns.

Tests were run to determine the optimal spacing between the electrodes. These tests were conducted on electrodes with spacing of 0.005, 0.01, 0.015, 0.02 and 0.03 inches, using Collagen, ADP and Ristocetin. Aggregation was measurable in all cases; however, 0.005, 0.01 and 0.015 gave the most reproducible results. Visual inspection showed a bigger platelet plug with 0.005, 0.01 and 0.015 than with 0.02 and 0.03. The most preferred embodiment is 0.01 in. spacing between the electrodes, because it is the center point of the spacing that worked best.

The electrodes can comprise any conductive material, such as steel, aluminum, precious metals and/or copper, with stainless steel being most preferred for its durability, corrosion resistance, conductivity and discardability based on its relatively low cost. A number of different stainless steel grades have been tested for use as electrodes according to the invention. Tempered hardened #316 stainless steel has been found to be particularly suitable, although other grades are also suitable.

The Cardinal et al. electrode assembly uses wires having a circular cross-section to measure platelet aggregation. The sample contacting portions of the electrodes (i.e., tips 7 and 8) of the present invention are non-circular in cross-section, preferably rectangular, and most preferably square. Tips having at least one planar face, such as square tips, allow the spacing to be uniform over the entire area between the electrode tips by positioning at least one planar face of one electrode tip adjacent and parallel to at least one planar face of the opposing electrode tip. Furthermore, square electrode tips are easier to produce than round electrode tips because a stamping process can be used to make the electrode out of flat metal to form an electrode plate (i.e., electrodes 3 and 4 of FIG. 1A).

Tests were run to determine the reproducibility of measurements generated by electrode tips having a square cross-section. The results of these tests indicate that the square tip electrode design has improved reproducibility over the round wire configuration.

Typical reproducibility of results using the old, rod-shaped electrodes versus rectangular electrodes according to the invention using the same sample and reagent concentration within a given set of tests are:

Rect shape (n=4) Average value 27.9 ohms, SD=2.25+/−8%

(n=4) Average value 18.7 ohms, SD=2.04+/−10%

Rod shaped (n=12) Average value 30.3 ohms, SD=4.16+/−14%

(n=13) Average value 30.1 ohms, SD=4.08+/−13.5%

Various sizes of electrodes were tested to find the ideal surface area to yield the same sensitivity as non-disposable electrodes presently being used. A thickness of 0.01 in. was selected so that the electrodes were rigid. In order to make the electrode pin square, it is also 0.01 in. wide. It was found from these experiments that a length of 0.2 in. provided a surface area which yielded results equivalent to non-disposable electrodes presently being used. The effective length or actual exposed length was 0.18 because some of the tip was covered by the outer sealing coating. A length of 0.1 to 0.3 will work, but the value of 0.18 gives results equivalent to presently used non-disposable electrodes. Shorter lengths give higher values, longer lengths give lower values. Therefore, the preferred electrodes tips are 0.01 inches square and 0.2 in. long, and the preferred exposed surface area of the tips is 0.0065 in$^2$.

As described above, square cross-sectioned electrode tips are most preferred. As best shown in FIG. 1A, the size and shape of the electrodes 3 and 4 above the tips 7 and 8 need not conform to the requirements for the tips 7 and 8, since the electrodes 3 and 4 only contact the sample at the tips 7 and 8 thereof. The portion of each electrode above the tip is coated with a non-conductive coating 9 to prevent contact with the sample, and the uncoated tabs 5 and 6 are not immersed in the sample.

The electrode tips 7 and 8 are preferably 0.01 inches square and 0.2 inches long. The figures depict preferred embodiments in which the width of each electrode above the tip increases from 0.01 inches to 0.1 inches (measured from left to right across each electrode from the perspective shown in FIG. 1A). This enlarged part of the electrode is covered with non-conductive material and thus does not contact the sample. See, e.g., FIG. 2. The width of each of the tabs 5 and 6 of the electrode is not critical, and can be, e.g., 0.65 inches (measured from left to right across each tab from the perspective shown in FIG. 1A).

The tabs 5 and 6 are connected to a circuit which detects the change in resistance between the electrodes as aggregation proceeds. To this end, it applies a known frequency AC voltage across a potential divider, one arm of which is formed by the test cell 100 (i.e., the loaded cuvette and electrode assembly) and produces an output, e.g., to a chart recorder, or analog to digital converter for digital output, representative of the resistance between the electrode tips 7 and 8. An alternating current is preferred to avoid polarization of the electrodes. Further details regarding the circuitry outside of the test cell and aggregometer data gathering and analysis can be found, e.g., in Cardinal et al.

The position of the electrode assembly 1 within the cuvette 10 can be removably or permanently fixed. FIGS. 2 and 3 show alternative preferred means for fixing the position of the electrode assembly within the cuvette 10.

FIG. 2 shows a positional clip 12, which contacts an internal wall of the cuvette 10 to fix the position of the electrode assembly 1. The clip can comprise, e.g., any inexpensive spring steel or copper. The semi-circular clip 12 is attached to the electrode assembly 1 just beneath the tabs 5 and 6 and extends outwardly from the electrode assembly 1 before returning to contact the midsection of the electrode assembly 1 at a point above the top of the sample in cuvette 10. As the cuvette 10 is preferably conical, narrowing from top to bottom, and the electrode assembly 1 with the clip 12 is made slightly larger than the diameter of the cuvette 10 at a point where the electrode assembly 1 is completely inserted, when the electrode assembly 1 is completely inserted into the cuvette 10 through the open top end thereof, the clip 12 wedges the electrode assembly 1 into a fixed position within the cuvette 10, as shown in FIG. 2.

The position fixing means shown in FIG. 3. are a pair of molded plastic, semi-circular fins 13 extending outwardly from the molded plastic coating 14 coated on the electrodes except at their tabs 5 and 6 and tips 7 and 8. The molded plastic can comprise any medical grade plastic which is nonreactive with blood samples. Polystyrene is a preferred material.

As best seen in FIGS. 4A and 4B, at least a portion of the outside edges of these fins 13, and at least a portion of the outside edges of the molded plastic coating 14 on the electrodes contact the walls of the cuvette 10 to fix the position of the electrode assembly 1 within the cuvette 10.

The aggregometer test cell 100 of the invention can be assembled as follows. Two electrodes 3 and 4 are positioned at a 180° angle to each other with the tabs 5 and 6 at the top and the tips 7 and 8 at the bottom, as shown in FIG. 1A. Between the electrode plates is inserted a preferably 0.01 in. thick insulator 2, which fixes the spacing between the electrodes 3 and 4, and electrically insulates them from each other. The preferred dimensions of the insulator 2 are 1.75×0.1×0.01 inches. The insulator 2 extends from the top of the electrode assembly 1, along the central axis of the electrode assembly 1 to a point just above the electrode tips 7 and 8. The insulator 2 does not extend between the electrode tips 7 and 8. The insulator 2 can comprise any insulative material, such as, e.g., teflon, mylar or plastics, with teflon being most preferred.

The electrodes 3 and 4 are fixed to the insulator by any suitable means which does not short circuit the insulator 2. It is preferred to fix the electrodes 3 and 4 to the insulator 2 by means of an adhesive substance or by mechanically fastening. Suitable adhesives include any electrically insulating adhesive, such as, e.g., epoxy. The electrodes 3 and 4 and insulator 2 can be mechanically fastened together with clips, nails, screws, and the like, provided that such hardware is non-conductive, or does not otherwise create a short circuit between the two electrodes 3 and 4. It is also possible to fasten the electrodes 3 and 4 to the insulator 2 merely by coating the central portion of the assembly 1 with a coating, such as the non-conductive plastic material 9 shown in FIG. 1B or the molded plastic coating 14 shown in FIG. 3.

After the insulator 2 and electrodes 3 and 4 are properly positioned (and preferably fixed by adhesive and/or mechanical means), the electrode assembly 1 is coated with a non-conductive material 9 between the tabs 5 and 6, and above the tips 7 and 8. The non-conductive material 9 must make a liquid tight seal, so that the sample only makes electrical contact with the electrode tips 7 and 8.

Another approach to producing the electrode assembly 1 is to provide a molded plastic coating 14 around the electrodes 3 and 4. The molded plastic coating 14 is liquid tight, ensuring that the sample only makes electrical contact with the electrode tips 7 and 8. The molded plastic coating 14 can be provided by seating the portion of the electrodes 3 and 4 between the tabs 5 and 6 and above the tips 7 and 8, with a spacer attached, into a mold and injecting plastic into the mold.

Still another approach to producing the electrode assembly 1 is to provide molded plastic parts with slots for the placement of the electrodes 3 and 4. After placing the electrodes 3 and 4 into the slots of a molded plastic part, a liquid-tight seal would be made around the electrode tips 7 and 8, preferably by sonic welding.

The electrodes can be inserted into a teflon extrusion that holds them in place and separated; this would then be inserted in an injection molding die to make the final assembly.

Regardless of how the electrode assembly is produced, the electrode tips 7 and 8 should sit in the location of optimum sample flow within the cuvette 10. The inventors have determined that this position is about halfway between the center of the cuvette and the cuvette wall, as shown in FIG. 4B. The plastic molding around the electrode plates is designed in such a way that, in conjunction with the fins 13, the electrode tips are fixed in the desired position, as discussed above.

EXAMPLES

The invention will be illustrated in more detail with reference to the following examples, but it should be understood that the present invention is not deemed to be limited thereto.

The assembled electrode is placed into a cuvette containing a sample of whole blood or diluted whole blood, PRP, washed platelets or other sample material. This sample is placed in a heater block and heated to a controlled temperature. The sample is stirred with a stirbar being spun at a rate of between 300 and 1200 rpm. When the electrode is first placed into the sample, a single layer of platelets builds up on the electrode tip.

An electronic circuit provides a small alternating electrical current to the electrode and monitors the current through the sample. As the initial layer of platelets builds up on the electrode tip, the current thorough the sample stabilizes and a baseline is established. An electronic circuit converts the current into an impedance measurement. After the baseline stabilizes, a gain is set on the electronic circuit by simulating a known impedance change.

A reagent which causes platelet aggregation is added to the sample. As the platelets aggregate, they gather on the electrode tip. This causes the current flowing between the electrode tips in the sample to be reduced, which is converted by the electronic circuit into a change of impedance. This change in impedance is related to the amount of platelet aggregation of the sample.

The change of impedance is recorded on a strip chart recorder, converted to a numeric readout of change of impedance in ohms or converted into data points which are sent to a computer system for interpretation and storage.

Test were run comparing the Cardinal et al. type electrode assembly to the present invention. Typical maximum aggregation readings in tests with the two types of electrodes are:

Cardinal et al. type electrode 20.8 ohms

Present invention electrode 22 ohms

Tests were also run to see if the present electrodes could detect dose response of reagent. Dose response curves were run with collagen as the reagent, varying the final collagen concentration in the sample, as follows:

| Final concentration | Maximum Aggregation |
| --- | --- |
| 4 micrograms/mL | 13.4 ohms |
| 2 micrograms/mL | 12.0 ohms |
| 1 microgram/mL | 9.4 ohms |
| 0.5 micrograms/mL | 1.2 ohms |

The disposable electrode according to the present invention yielded equivalent results to those obtained using a non-disposable electrode according to Cardinal et al. The results obtained using the present invention are reproducible from electrode to electrode. The low cost of the electrode and the reproducibility of the results makes it feasible for electrodes according to the invention to be disposable.

While the invention has been described in detail and with reference to specific examples thereof, it will be apparent to one skilled in the art that various changes and modifications can be made therein without departing from the spirit and scope thereof.

What is claimed is:

1. An aggregometer comprising an electrode assembly comprising:

two opposing electrodes adapted to measure platelet aggregation as a function of impedance within a sample containing platelet, each of said electrodes comprising a tab, a shaft and a tip, and each of said electrodes having a non-circular cross-section, and an insulator sandwiched between said shafts of said two opposing electrodes, wherein a planar surface of a first said electrode tin is substantially parallel to an adjacent planar surface of a second said electrode tip to provide a channel which the sample flows through during platelet aggregation.

2. The aggregometer according to claim 1, wherein said cross-section is rectangular.

3. The aggregometer according to claim 1, wherein said cross-section is square.

4. The aggregometer according to claim 1, wherein said opposing electrodes are self-supporting.

5. The aggregometer according to claim 4, wherein the first and second electrode tips are 0.005 to 0.015 in. apart.

6. The aggregometer according to claim 5, wherein the first and second electrode tips are about 0.01 in. apart.

7. The aggregometer according to claim 5, wherein the first and second electrode tips each has a surface area of 0.0041 to 0.0121 in$^2$.

8. The aggregometer according to claim 5, wherein the first and second electrode tips each has a surface area of about 0.0065 in$^2$.

9. The aggregometer according to claim 5, wherein each of the first and second electrode tips is about 0.01 in. long, 0.01 in. wide and 0.2 in. high.

10. The aggregometer according to claim 1, wherein the electrode tips comprise stainless steel.

11. An aggregometer comprising:

a cuvette for holding a platelet-containing sample;

an electrode assembly attached to said cuvette, said electrode assembly comprising (i) two opposing electrodes for measuring it impedance within the sample, each of said electrodes comprising a tab, a shaft and a tip, (ii) an insulator sandwiched between said shafts of said two opposing electrodes, and (iii) a non-conductive water resistant coating on said shaft of said electrodes and said insulator, wherein a planar surface of a first said electrode tip is substantially parallel to an adjacent planar surface of a second said electrode tip, and wherein said electrode tips are positioned within said cuvette such that when said platelet containing sample is loaded into and circulated about said cuvette, said electrode tips are immersed within said sample and said adjacent planar surfaces of said electrode tips form a channel which is substantially parallel to a flow direction of said sample prior to entering said channel;

a stirring device for circulating said sample within said cuvette so as to create relative movement between said sample and said electrode tips;

a power source for supplying an electric current to said electrode assembly; and a data analysis device for receiving and analyzing data from said electrode assembly.

12. A method for analyzing platelet aggregation in a sample, said method comprising:

providing said sample containing platelets;

providing an aggregometer according to claim 11;

placing said sample in said cuvette of said aggregometer;

actuating said aggregometer to establish a baseline impedance measurement;

adding to said sample a reagent which causes platelet aggregation;

detecting a change in impedance in said sample containing said reagent; and analyzing said platelet aggregation in said sample based on said impedance change.

13. The method according to claim 12, wherein prior to adding said reagent, said sample comprises at least one member selected from the group consisting of whole blood, diluted whole blood, platelet-rich plasma and washed platelets.

14. The method according to claim 13, wherein prior to adding said reagent, said sample consists essentially of whole blood.

15. The method according to claim 13, wherein said sample, cuvette and electrode assembly are discarded after said platelet aggregation analysis.

* * * * *